United States Patent [19]

Adachi et al.

[11] Patent Number: 4,496,717
[45] Date of Patent: Jan. 29, 1985

[54] ERYTHROMYCIN B DERIVATIVES

[75] Inventors: Takashi Adachi, Kuki; Shigeo Morimoto, Saitama; Yoko Takahashi, Ageo; Yoshiaki Watanabe, Kodaira; Sadafumi Omura, Ageo, all of Japan

[73] Assignee: Taisho Pharmaceutical Co., Ltd., Tokyo, Japan

[21] Appl. No.: 444,170

[22] Filed: Nov. 24, 1982

[30] Foreign Application Priority Data

Dec. 1, 1981 [JP] Japan .................. 56-193444

[51] Int. Cl.³ .......................... C07H 17/08
[52] U.S. Cl. .................................. 536/7.2
[58] Field of Search .......................... 536/7.2

[56] References Cited

U.S. PATENT DOCUMENTS 3,884,904  5/1975  Jones et al. ............ 424/180
4,331,803  5/1982  Watanabe et al. ............ 536/7.2

Primary Examiner—Johnnie R. Brown
Assistant Examiner—Elli Peselev
Attorney, Agent, or Firm—George A. Loud

[57] ABSTRACT

Novel erythromycin B derivatives of the formula

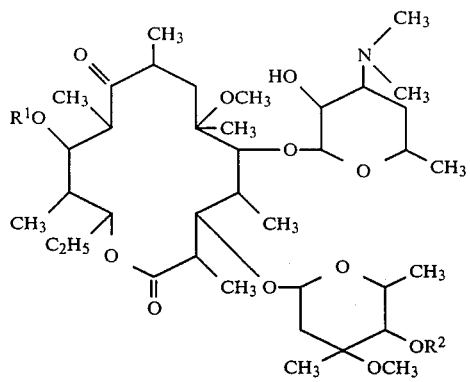

wherein $R^1$ and $R^2$ are the same or different and are each hydrogen or methyl, and the pharmaceutically acceptable acid addition salts thereof are disclosed. They exhibit excellent in vivo antibacterial activity against Gram-positive bacteria.

4 Claims, No Drawings

ERYTHROMYCIN B DERIVATIVES

The present invention relates to novel antibacterial agents. More specifically, it is concerned with novel erythromycin B derivatives which possess in vivo antibacterial activity against Gram-positive bacteria.

The present invention is based on the discovery that new derivatives of erythromycin B whose one to three hydroxy groups are methylated exhibit higher in vivo antibacterial activity than other closely analogous compounds such as erythromycin B against Gram-positive bacteria.

The compounds of the present invention are an erythromycin B derivative of the formula

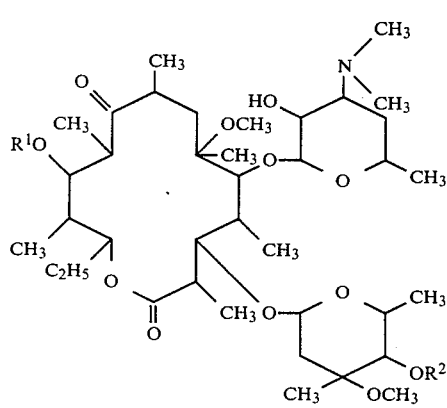

wherein $R^1$ and $R^2$ are the same or different and are each hydrogen or methyl, and the pharmaceutically acceptable acid addition salts thereof.

Most preferred compound of the present invention is that of formula I wherein both of $R^1$ and $R^2$ are hydrogen atoms.

The pharmaceutically acceptable acid addition salts of the compounds of formula I include salts with inorganic acids such as hydrochloric acid, hydrobromic acid, hydroiodic acid, nitric acid, sulfuric acid, sulfurous acid, phosphoric acid and the like, or organic acids such as formic acid, acetic acid, propionic acid, butyric acid, lactic acid, citric acid, malic acid, glycolic acid, tartaric acid, succinic acid, maleic acid, fumaric acid, gluconic acid, stearic acid, mandelic acid, benzoic acid, methanesulfonic acid, aminoethanesulfonic acid, p-toluenesulfonic acid, glutamic acid, aspartic acid and the like.

The compound of formula I may be prepared, for example, by the following processes:

(1) Erythromycin B is gradually added to a vigorously stirred mixture of excess carbobenzoxy chloride and a base, and then the mixture is stirred for 1–3 hours at room temperature to 60° C. After filtration, the filtrate is purified in a conventional manner to give a compound of the formula

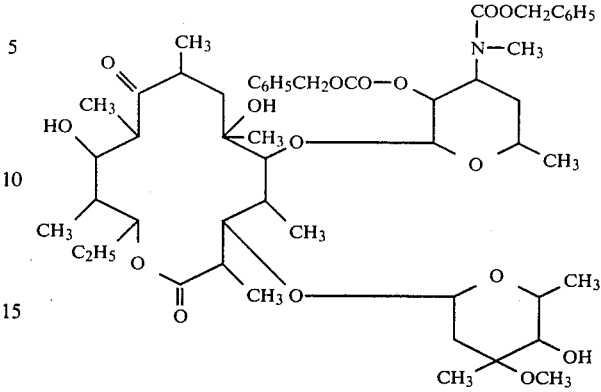

Examples of the base are sodium bicarbonate, potassium bicarbonate and the like.

(2) The compound of formula II is reacted with a methylating agent such as methyl iodide, dimethyl sulfate and the like in the presence of a suitable base in a solvent in order to effect methylation of one to three of the hydroxy groups at the 6-, 11- and 4''-positions of the compound of formula II. The reaction mixture is worked up in a conventional manner to give a compound of the formula

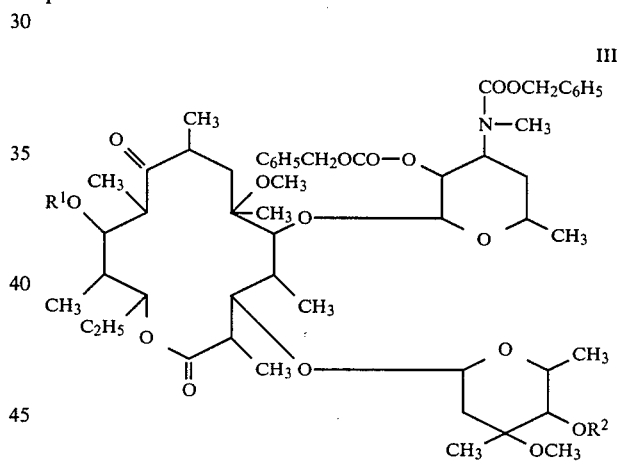

wherein $R^1$ and $R^2$ are as defined above.

5–10 moles of the methylating agent per mole of the compound of formula II may be used for methylation.

Examples of the suitable base are alkali metal hydrides such as sodium hydride, potassium hydride and the like, alkali metal amides such as lithium amide, sodium amide and the like, butyl lithium, lithium diisopropylamide and the like.

When used 1.5–2.0 moles of the base per mole of the compound of formula II at $-10°$–$5°$ C., preferably $-5°$14 0° C. for methylation, there is obtained a compound of formula III wherein both of $R^1$ and $R^2$ are hydrogen atoms.

When used 2.5–3.0 moles of the base per mole of the compound of formula II at 0° C. to room temperature for methylation, there is obtained a compound of formula III wherein $R^1$ is hydrogen atom and $R^2$ is methyl group.

When used 3.5–4.0 moles of the base per mole of the compound of formula II at 3° C. to room temperature, there is obtained a compound of formula III wherein both of $R^1$ and $R^2$ are methyl groups.

Examples of the solvent used for methylation are polar aprotic solvents such as N,N-dimethylformamide, N,N-dimethylacetamide, dimethylsulfoxide, hexamethylphosphoric triamide, preferably N,N-dimethylformamide or a mixture of dimethylsufoxide and tetrahydrofuran.

The compound of formula III thus obtained may be provided without isolation in the next reaction, or may be isolated by silica gel chromatography.

(3) The compound of formula III is subjected to catalytic reduction according to the method reported by E. H. Flynn et al. in Journal of the American Chemical Society, 77, page 3104(1955) in order to eliminate the protecting group of benzyloxycarbonyl, and subjected to catalytic reduction in the presence of excess formaldehyde to effect N-methylation, giving the compound of formula I.

The intermediate obtained by catalytic reduction for the above elimination may be used without isolation, or after isolation in a conventional manner for N-methylation.

Purification of the compound of formula I may be carried out by recrystallisation or column chromatography.

The pharmaceutically acceptable acid addition salt of the compound of formula I may be obtained by treating the compound of formula I with one mole equivalent of the corresponding acid described above in an inert solvent such as water, acetone, methanol and ethanol. The salts thus obtained are collected by filtration if they are insoluble in the inert solvent, by precipitation by addition of a non-solvent for the salt, or by evaporation of the solvent.

The compounds of the present invention have excellent in vivo antibacterial activity against Gram-positive bacteria, therefore, they can be used as the antibacterial agents in mammals. For these purposes, a compound of formula I may be administered orally or parenterally in a conventional dosage form such as tablet, capsule, powder, troche, dry mixes, ointment, suspension or solution prepared according to conventional pharmaceutical practices.

The compounds of formula I can be administered at a dosage of from about 1 mg/kg to about 100 mg/kg of body wight per day. The preferred dosage range is from about 2 mg/kg to about 25 mg/kg of body weight per day.

The compounds of the present invention have excellent low toxicity. The $LD_{50}$ value in mice is in excess of 5000 mg/kg of body weight.

The present invention is further illustrated by the following examples.

EXAMPLE 1

In a mixture of 6.0 ml of carbobenzoxy chloride and 4.0 g of sodium bicarbonate was added 2.0 g of erythromycin B in small portions with stirring at 45° C. The mixture was stirred for 1.5 hours at the same temperature, and 10 ml of dichloromethane was added. Stirring was continued for a further 5 minutes, the reaction mixture was filtrated, and the residue was washed with dichloromethane. The filtrate and the washes were combined, and concentrated to dryness. The resulting residue was recrystallized from a mixture of chloroform and ether to give 2.60 g of 2'-O-benzyloxycarbonyl-N-benzyloxycarbonyl-des-N-methylerythromycin B as colorless needles.

m.p. 212°–213.5° C.

Elemental analysis (for $C_{52}H_{77}NO_{16}$): Calcd. (%): C, 64.24; H, 7.98; N, 1.44. Found. (%): C, 63.96; H, 8.03; N, 1.35.

Mass (m/e): 971 (M+)

IR $\nu_{max}^{KBr}$ cm$^{-1}$: 3490, 1754, 1728, 1700.

$^1$H-NMR(CDCl$_3$): δ=2.82, 2.86(3H), 5.05–5.22(4H), 7.26–7.48(m, 10H).

In 8 ml of a mixture of dry dimethylsulfoxide and dry tetrahydrofuran (1:1) were dissolved 1.0 g of 2'-O-benzyloxycarbonyl-N-benzyloxycarbonyl-des-N-methylerythromycin B and 1.0 ml of methyl iodide. The solution was stirred under cooling at −5° C.-0° C. in a nitrogen stream and 80 mg of 55–65% sodium hydride dispersion was added thereto in small portions. Stirring was continued for a further 15 minutes at the same temperature to complete the reaction.

After completion of the reaction, 1.5 ml of triethylamine was added with stirring under ice-cooling, and the reaction mixture was poured into a saturated aqueous sodium bicarbonate solution. This was extracted with ethyl acetate, and the extract was washed with a saturated aqueous sodium chloride solution, and dried over anhydrous magnesium sulfate.

Evaporation of the solvent gave the crude product, which was then dissolved in a mixture of 35 ml of ethanol and 7 ml of a 2.5M acetic acid buffer solution (pH 5.0). To the solution was added 300 mg of palladium black, and the mixture was stirred for 5 hours at ambient temperature under atmospheric pressure in a gentle hydrogen stream in order to effect catalytic reduction. Into the resulting mixture was poured 7 ml of 35% aqueous formaldehyde, and catalytic reduction was continued for a further 2 hours.

After completion of the reaction, the catalyst was filtered off and the filtrate was concentrated to dryness in vacuo. To the resulting residue was added an aqueous sodium bicarbonate solution. Extraction was carried out with ethyl acetate, and the resulting organic layer was washed with an aqueous sodium chloride solution, and dried over anhydrous sodium sulfate. After evaporation of the solvent, the resulting residue was applied on a silica gel column chromatography (silica gel for column chromatography produced by E. Merck Darmstadt, 70–230 mesh, and a mixture of chloroform and methanol(10:1) as a developing solvent), and the fractions obtained was collected.

Thin layer chromatography (silica gel 60 $F_{254}$ produced by E. Merck Darmstadt, and a mixture of chloroform and methanol(3:1) as a developing solvent) was applied to the detection of the product for each fraction, the fractions having a spot at Rf value of 0.37 were collected (cf., Rf value of erythromycin B, 0.33), and the solvent was evaporated in vacuo to give a foam. Recrystallization from a mixture of chloroform and n-hexane gave 516 mg of 6-O-methylerythromycin B as crystals.

m.p. 219°–220° C.

Elemental analysis (for $C_{38}H_{69}NO_{12}$): Calcd. (%): C, 62.36; H, 9.50; N, 1.91. Found. (%): C, 62.70; H, 9.40; N, 1.74.

Mass (m/e): 731 (M+).

IR $\nu_{max}^{CHCl_3}$ cm$^{-1}$: 3460, 1732, 1694.

$^1$H-NMR(CDCl$_3$): δ=2.31(s, 6H), 3.11(s, 3H), 3.35(s, 3H).

EXAMPLE 2

In 6.4 ml of dry N,N-dimethylformamide were dissolved 0.8 ml of methyl iodide and 0.80 g of 2'-O-benzyloxycarbonyl-N-benzyloxycarbonyl-des-N-methylerythromycin B. The solution was stirred under cooling at 0°–5° C., and 80 mg of 55–65% sodium hydride dispersion was added thereto in small portions with stirring.

Then, the temperature was allowed to raise to room temperature, and stirring is continued for a further 30 minutes, and working up was carried out by the similar method to that of Example 1.

The crude product thus obtained was applied to a silica gel column chromatography using a mixture of n-hexane and ethyl acetate(3:1) as a developing solvent, and the fractions were collected. Silica gel thin layer chromatography (the same thin layer chromatography plate, and a mixture of n-hexane and ethyl acetate(1:2) as a developing solvent) was applied to the detection of the product for each fraction, the fractions having a spot at Rf value of 0.61 were collected (cf., Rf value of starting compound, 0.28), and the solvent was evaporated in vacuo to give 420 mg of the crude product.

600 mg of the crude product thus obtained was dissolved in a mixture of 21 ml of ethanol and 4.2 ml of 2.5M acetic acid buffer solution (pH 5.0), to which was added 300 mg of palladium black. Catalytic reduction was carried out by the similar method to that of Example 1. Subsequently, the resulting reaction mixture was subjected to reductive methylation using 4.2 ml of 35% aqueous formaldehyde solution, and worked up according to the similar method to that of Example 1. The residue thus obtained was then purified by column chromatography (silica gel for column chromatography produced by E. Merck Darmstadt, 70–230 mesh; and a mixture of chloroform and methanol(10:1) as a developing solvent) to give a foam.

Recrystallization from chlorofrom gave 327 mg of 6,4''-di-O-methylerythromycin B as crystals.

m.p. 203.5°–205.5° C.

Elemental analysis (for $C_{39}H_{71}NO_{12}$) Calcd. (%): C, 62.79; H, 9.60; N, 1.88. Found. (%) C, 62.42; H, 9.40; N, 1.77.

Mass (m/e): 745 (M+).

IR $\nu_{max}^{KBr}$ cm$^{-1}$: 3420, 1728, 1690.

$^1$H-NMR(CDCl$_3$): $\delta$=2.30(s, 6H), 3.12(s, 3H), 3.34(s, 3H), 3.56(s, 3H).

EXAMPLE 3

In 8 ml of dry N,N-dimethylformamide were dissolved 1.0 g of 2'-O-benzyloxycarbonyl-N-benzyloxycarbonyl-des-N-methylerythromycin B and 1.0 ml of methyl iodide. The solution was stirred under cooling at 3°–5° C., and 192 mg of 55–65% sodium hydride dispersion was added thereto in small portions. The mixture was submitted for the same reduction as described in Example 1 to give the crude product, which was purified by the same silica gel column chromatography in Example 2, except for the use of a mixture of n-hexane and ethyl acetate(1:1) in place of one(1:2) to give 972 mg of a foam.

830 mg of the foam was treated by the similar method to that of Example 1, and the crude product thus obtained was purified by the same silica gel column chromatography, except for the use of a mixture of chloroform and methanol(20:1) in place of one(10:1) to give a foam. Recrystallization from a mixture of dichloromethane and petroleum ether gave 316 mg of 6, 11, 4''-tri-O-methylerythromycin B as crystals.

m.p. 231°–232° C.

Elemental analysis (for $C_{40}H_{73}NO_{12}$) Calcd. (%): C, 63.21; H, 9.68; N, 1.84. Found. (%): C, 62.23; H, 9.64; N, 1.67.

Mass (m/e): 759 (M+).

IR $\nu_{max}^{KBr}$ cm$^{-1}$: 3460, 1725.

$^1$H-NMR(CDCl$_3$): $\delta$=2.28(s, 6H), 3.17(s, 3H), 3.34(s, 3H), 3.45(s, 3H), 3.55(s, 3H).

The following experiment illustrates in vivo antibacterial activity of the compound of the present invention.

EXPERIMENT

Male ddY mice weighing 20–23 g in groups 16 each were inoculated with *Staphylococcus aureus* Smith No. 4 ($10^7$ cells per mouse, i.p.). Erythromycin B was used as a control, the compound of formula I wherein both of $R^1$ and $R^2$ are hydrogen atoms("compound 1") was administered orally at one hour after inoculation, and the number of living mice seven days after administration was calculated to determine the in vivo antibacterial activity. The results are shown in the following table.

| dose (mg/mouse) | In vivo Antibacterial Activity [The Number of Surviving Mice] Test Compound | |
|---|---|---|
| | Compound 1 | Erythromycin B |
| 2 | 16 | 16 |
| 1 | 16 | 10 |
| 0.5 | 10 | 4 |

What is claimed is:

1. An erythromycin B derivative of the formula

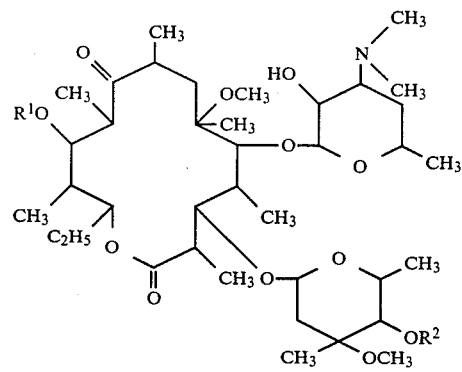

wherein $R^1$ and $R^2$ are the same or different and are each hydrogen or methyl, and the pharmaceutically acceptable acid addition salts thereof.

2. A compound according to claim 1 wherein both of $R^1$ and $R^2$ are hydrogen atoms.

3. A compound according to claim 1 wherein $R^1$ is hydrogen atom, and $R^2$ is methyl group.

4. A compound according to claim 1 wherein both of $R^1$ and $R^2$ are methyl groups.

* * * * *

UNITED STATES PATENT AND TRADEMARK OFFICE
CERTIFICATE OF CORRECTION

PATENT NO. : 4,496,717

DATED : January 29, 1985

INVENTOR(S) : Takashi ADACHI, Shigeo MORIMOTO, Yoko TAKAHASHI, Yoshiaki WATANABE, and Sadafumi OMURA It is certified that error appears in the above—identified patent and that said Letters Patent is hereby corrected as shown below:

Col. 1, line 16, delete "an"
       line 17, delete "derivative" insert --derivatives--
       line 41, delete "most" insert --The most--
       line 46, delete "with" insert --of--
       line 49, delete "or" insert --and--
       line 60, delete in its entirety and substitute --example, as follows:--

Col. 2, line 19, delete "the base" insert --suitable bases--
       line 24, delete "and" insert --or--
       line 51, delete "the"; same line, delete "base" insert --bases--
       line 56, delete "used" insert --using--
       line 60, delete "of"
       line 62, delete "used" insert --using--
       line 65, after "is" (both occurrences) insert --a-- respectively
       line 67, delete "used" insert --using--

Col. 3, line 2, delete "of"
       line 3, after "solvent" insert --which may be--
       line 10, delete "provided" insert --transferred-- and delete "in" insert --to--
       line 22, after "manner" insert a comma --,--
       line 27, delete "The" insert --A--
       line 31, delete "and" insert --or--
       line 40, delete "these purposes" insert --this purpose--
       line 43, delete "mixes" insert --mix--
       line 48, delete "wight" insert --weight--
       line 58, delete "In" insert --To--
       line 60, delete "portions" insert --increments--
       line 64, delete "filtrated" insert --filtered--

UNITED STATES PATENT AND TRADEMARK OFFICE
CERTIFICATE OF CORRECTION

PATENT NO. : 4,496,717

DATED : January 29, 1985

INVENTOR(S) : Takashi ADACHI, Shigeo MORIMOTO, Yoko TAKAHASHI, Yoshiaki WATANABE, and Sadafumi OMURA It is certified that error appears in the above-identified patent and that said Letters Patent is hereby corrected as shown below:

Col. 4, line 16, before "55 -" insert --a--
      line 17, delete "portions" insert --increments--
      line 34, before "35 %" insert --a--
      line 35, after "formaldehyde" insert --solution--
      line 50, delete "was" insert --were--
      line 54, delete "to" insert --for-- and delete "for" insert --in--

Col. 5, line 8, delete "portions" insert --increments--
      line 11, delete "is" insert --was--
      line 12, delete "by the" insert --in a manner--
      line 13, delete "method"
      line 18, delete "chromatography" insert "chromatograph--
      line 20, delete "to" insert --for--
      line 29, delete "by the" and "method"
      line 31, before "35" insert --a--
      line 32, delete "accord-"
      line 33, delete "ing to the" insert --in a manner--; same line, delete "method"
      line 56, delete "portions" insert --increments--
      line 59, delete "chromatography" insert --chromatograph as--

UNITED STATES PATENT AND TRADEMARK OFFICE
CERTIFICATE OF CORRECTION

PATENT NO. : 4,496,717

DATED : January 29, 1985

INVENTOR(S) : Takashi ADACHI, Shigeo MORIMOTO, Yoko TAKAHASHI, Yoshiaki WATANABE, and Sadafumi OMURA It is certified that error appears in the above—identified patent and that said Letters Patent is hereby corrected as shown below:

Col. 6, line 61, delete "atoms"
        line 63, delete "group"
        line 65, delete "groups"

Signed and Sealed this

Fifteenth Day of October 1985

[SEAL]

Attest:

DONALD J. QUIGG

Attesting Officer

Commissioner of Patents and Trademarks—Designate